United States Patent
Boodaghians et al.

(10) Patent No.: US 9,260,323 B2
(45) Date of Patent: Feb. 16, 2016

(54) POINT OF USE WATER TREATMENT DEVICE

(71) Applicant: MAG Aerospace Industries, LLC, Carson, CA (US)

(72) Inventors: Razmik B. Boodaghians, Glendale, CA (US); Shane Nazari, Glendale, CA (US)

(73) Assignee: MAG Aerospace Industries, LLC, Carson, CA (US)

( * ) Notice: Subject to any disclaimer, the term of this patent is extended or adjusted under 35 U.S.C. 154(b) by 0 days.

(21) Appl. No.: 14/533,208

(22) Filed: Nov. 5, 2014

(65) Prior Publication Data

US 2015/0129776 A1    May 14, 2015

Related U.S. Application Data

(60) Provisional application No. 61/901,741, filed on Nov. 8, 2013.

(51) Int. Cl.
*A61L 2/10* (2006.01)
*C02F 1/32* (2006.01)

(52) U.S. Cl.
CPC . *C02F 1/325* (2013.01); *A61L 2/10* (2013.01); *C02F 2201/001* (2013.01); *C02F 2201/004* (2013.01); *C02F 2201/328* (2013.01); *C02F 2201/3222* (2013.01); *C02F 2201/3227* (2013.01); *C02F 2201/3228* (2013.01); *C02F 2303/04* (2013.01); *C02F 2307/06* (2013.01)

(58) Field of Classification Search
USPC .......... 250/453.11, 454.11, 455.11, 428, 431, 250/432 R, 436; 422/22, 23, 24
See application file for complete search history.

(56) References Cited

U.S. PATENT DOCUMENTS

| | | | |
|---|---|---|---|
| 4,871,452 | A | 10/1989 | Kohler et al. |
| 6,143,185 | A | 11/2000 | Tracy et al. |
| 8,742,364 | B2 | 6/2014 | Boodaghians et al. |
| 2012/0051977 | A1 | 3/2012 | Boodaghians et al. |
| 2013/0146783 | A1 | 6/2013 | Boodaghians et al. |
| 2014/0264072 | A1* | 9/2014 | Abbott .............. A61M 16/1055 250/438 |

FOREIGN PATENT DOCUMENTS

| | | |
|---|---|---|
| KR | 20110038896 A | 4/2011 |
| WO | 2006134567 A1 | 12/2006 |
| WO | 2013152485 A1 | 10/2013 |
| WO | 2013176736 A1 | 11/2013 |
| WO | 2014187523 A1 | 11/2014 |

OTHER PUBLICATIONS

International Patent Application No. PCT/US2014/063992, Search Report and Written Opinion dated Jan. 26, 2015.

* cited by examiner

*Primary Examiner* — Nicole Ippolito
(74) *Attorney, Agent, or Firm* — Kilpatrick Townsend & Stockton LLP; Dean W. Russell; Kristin M. Crall

(57) ABSTRACT

Embodiments of the present invention provide a water treatment device that can treat water at its point of use. For example, the water treatment device may be positioned at or near a faucet outlet, so that water can be treated immediately before it leaves the faucet. The water treatment device may be a water treatment reactor with a plurality of UV LEDs positioned between a shield and a heat sink component.

12 Claims, 4 Drawing Sheets

POINT OF USE WATER TREATMENT DEVICE

CROSS REFERENCE TO RELATED APPLICATIONS

This application claims the benefit of U.S. Provisional Application Ser. No. 61/901,741, filed Nov. 8, 2013, titled "UV Point of Use Water Treatment Mini Reactor," the entire contents of which are hereby incorporated by reference.

FIELD OF THE DISCLOSURE

Embodiments of the present disclosure relate generally to a water treatment device that can treat water at its point of use. For example, the water treatment device may be positioned at or near a faucet outlet, so that water can be treated immediately before it leaves the faucet. The water treatment device may be a water treatment reactor with a plurality of UV LEDs positioned between a shield and a heat sink component.

BACKGROUND

Disinfection of water on-board passenger transportation vehicles is necessary to guarantee water quality. This may include disinfection of potable water that is delivered to beverage makers, water that is delivered to sinks for hand-washing, water that is delivered to toilets for flushing, or water that is otherwise routed on-board the vehicle for various forms of use or consumption. For example, water systems on aircraft are complicated systems that usually include a tank with plumbing conduits and a pressurization system to deliver water to the points of use.

The issue of water quality, and in particular, of potable water quality, on passenger transportation vehicles and equipment, such as aircraft, trains, boats and ships, and the like is a point of interest for regulatory authorities. Regulatory standards have been enacted that require carried water on-board passenger vehicles to be disinfected according to certain standards. Passenger airlines and other transportation companies must thus implement appropriate aircraft water disinfection protocols.

U.S. Pat. No. 4,871,452 to Kohler, et al., entitled "On-Board Water Supply," discloses equipment for purifying waste water from galleys, sinks, and toilets of aircraft. Waste water from these areas discharges to a tank, after which it passes through a mechanical filter, a bed of active carbon, ozone and osmotic stages, and a disinfection stage involving addition of chlorine and irradiation with ultraviolet ("UV") light. Thereafter, the water is made available to aircraft passengers for certain uses.

U.S. Pat. No. 6,143,185 to Tracy, et al. entitled "Treatment System for Aircraft Toilet Waster Water" discloses alternate systems for decontaminating waste water from aircraft toilets, sinks, and galleys. They too include a mechanical particulate filter, activated carbon, and a source of UV light. Alternatively, according to the Tracy patent, the waste water may be exposed to microwaves or treated with chlorine or iodine. A sensor may be used to measure "the level of clarity of the treated water as an indication of its purity" and restrict opening of a control valve until acceptable clarity levels are obtained.

However, these systems and methods are primarily directed at purifying wastewater removed from the aircraft. Airlines and other passenger transport vehicle companies must also ensure that the potable water (i.e., drinkable water) aboard the aircraft is fit for human consumption by employing appropriate disinfection protocols. Disinfection upon upload and periodic disinfection sampling does not always adequately address the issue of contamination introduced in uploaded water, which is of particular concern for aircraft flying to and from, and being serviced in, non-industrialized areas. In addition, air must be introduced into the water storage and dispensing system on the aircraft in order to maintain pressurization, as well as to drain the system during routine servicing. This air can introduce pathogens that can multiply and cause unsanitary conditions and unacceptable water quality in the intervals between samplings or disinfection procedures. In effect, because the water storage and dispensing system is routinely exposed to the outside environment, potable water quality cannot always be ensured without some form of additional treatment. There is thus a need to further disinfect the water once it has been circulating in the aircraft water pipe system for a period of time, as the water may also need to be treated on an on-going basis, particularly as it is being delivered to the point of use.

Continuous treatment of potable water supplies presents its own set of potential problems to be solved, including continuous or semi-continuous dosing of the water with the requisite dosing equipment (metering and monitoring equipment, dosing agent storage equipment, and/or equipment for in-situ generation of the dosing agent). Accordingly, attempts have been made to purify water while on-board an aircraft or other passenger vehicles directly at the point of use. For example, U.S. Pat. No. 8,568,585 to Nolan entitled "Water Distribution System With Dual Use Water Treatment Unit" discloses systems for treating water by irradiation with UV lamp, along with an activated carbon or sediment filter.

Ultraviolet treatment eliminates bacteria, viruses, spores, and mold in the water and works similar to the way that strong sunlight can permanently purify water by making biological impurities inactive. Ultraviolet lamps are generally designed to destroy the links in these micro-organisms' DNA so that they are de-activated and cannot reproduce. The crucial hydrogen bonds that link the DNA chain together rupture when exposed to light between the wavelengths of about 220 nm to about 310 nm.

There are a number of water treatment solutions being employed and/or studied for use on-board aircraft. For example, one way that water can be treated is via UV mercury lamps. These lamps deliver an ultraviolet light to the water in the system and have been found beneficial because the treatment does not change the taste or odor of the water, it kills bacteria, viruses and protozoan, it is compact and easy to use, and it can prevent biofilm if the system is kept clean. However, one of the disadvantages of mercury UV lamps for water treatment is that they require a medium to high electrical demand, which means that when used on-board a vehicle such as an aircraft, they pull electrical power from the aircraft engines and/or an auxiliary power unit (APU). Increased usage of aircraft power from the engines results in higher fuel consumption and costs. Other disadvantages are that UV mercury lamps require cleaning and new lamps annually, and if a mercury lamp is broken, there exists a chance for mercury contamination of the water to be treated. Additionally, UV lamps take a while to power on if not in constant use. For UV lamps, the highest peak is generally mono-chromatic, in that the lamps generally only emit one effective wavelength, which is usually 254 nm for water treatment.

A further method of water treatment that has been explored is the use of ultraviolet light emitting diode (UV LED) light for water treatment. In addition to the mercury lamp benefits, the use of UV LED light also has the advantage of being able to use a wider UV band with multiple LED wavelengths, and it can offer a high power output with less power consumption than UV lamps. UV LEDs have greater longevity, power up quickly without requiring a delay time built into the system for the UV light source to reach its optimum UV energy output, and do not contain mercury. Some companies have been manufacturing UV lamps and LED systems for water sanitation and disinfection, but none of the available systems are designed for use on-board a transportation vehicle or an aircraft.

Therefore, a current need exists for a UV LED system for use in a vehicle or aircraft environment that is space efficient, energy efficient, accessible, and that is located in close proximity to a power supply and a water-system plumbing. It is also desirable to provide a system that can be added to existing systems, as opposed to having to replace the entire plumbing system on the vehicle.

BRIEF SUMMARY

Embodiments described herein thus provide a UV LED water treatment device that can treat water at its point of use. For example, the water treatment device may be positioned at or near a faucet outlet, so that water can be treated immediately before it leaves the faucet. The water treatment device may be a water treatment reactor with a plurality of UV LEDs positioned between a shield and a heat sink component.

In one example, there is provided a water treatment reactor device, comprising: a treatment chamber; a first set of ultraviolet light emitting diodes positioned at one end of the treatment chamber, and a second set of ultraviolet light emitting diodes positioned at an opposite end of the treatment chamber; each of the first and second sets of ultraviolet light emitting diodes being supported by first and second end caps; the first end cap comprising an inlet for receiving water to be treated, the second end cap comprising an outlet for exit of treated water; each of the end caps further comprising a shield secured in front of the ultraviolet light emitting diodes and a heat sink secured behind the ultraviolet light emitting diodes.

DETAILED DESCRIPTION

Embodiments of the present disclosure provide a water treatment device that is designed to treat water at its point of use. The embodiments described herein may be used in connection with the systems described in co-owned U.S. Pat. No. 8,742,364 to Boodaghians, titled "Systems and Methods for Disinfecting Water," as well as in co-owned U.S. Publication No. 2013/0146783 to Boodaghians, titled "Inline UV LED Water Disinfection and Heating."

Figure 1:
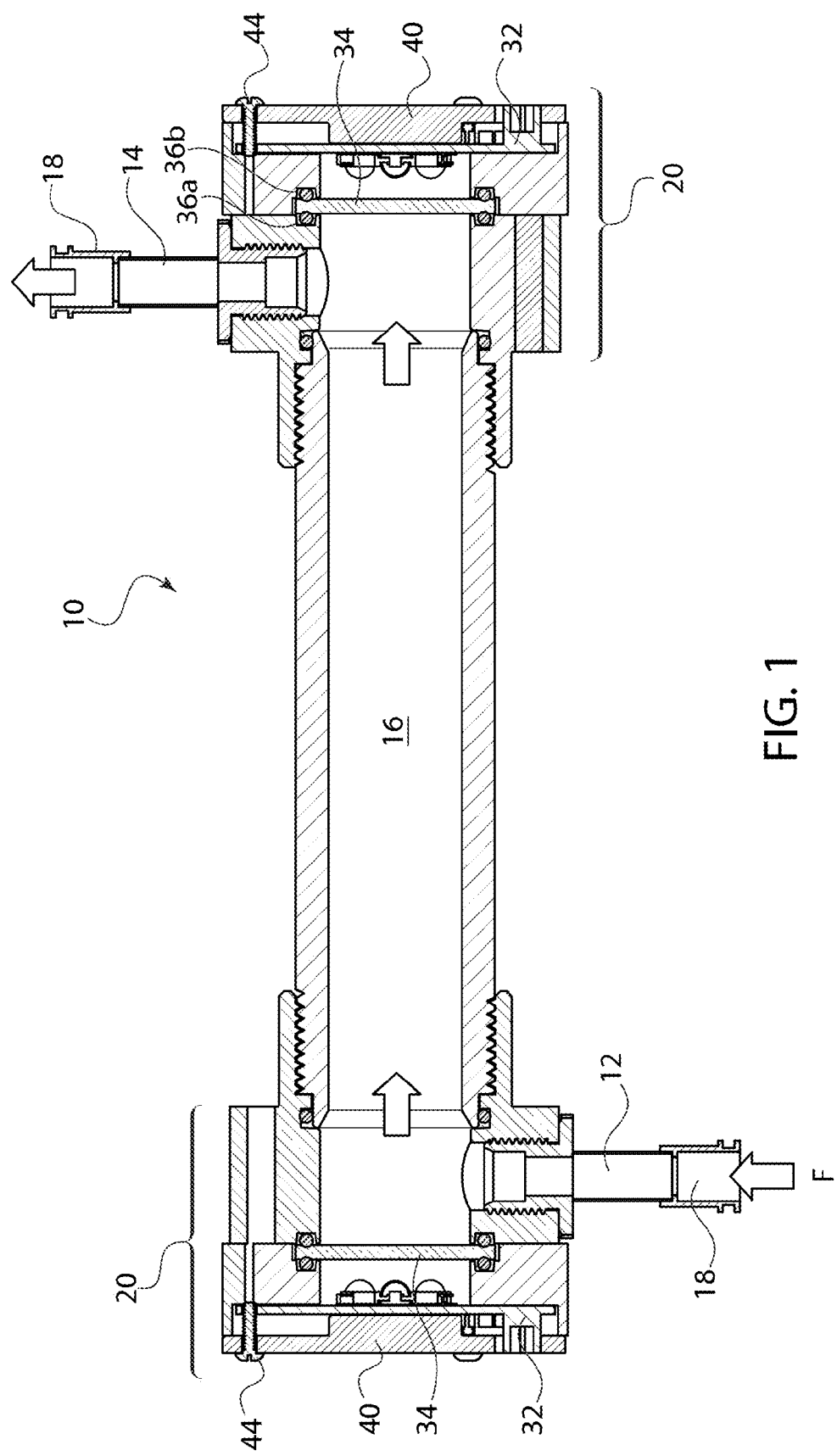
FIG. 1 shows a side cross-sectional view of a water treatment device.

As shown in FIG. 1, there is provided a water treatment reactor device 10 that receives a flow "F" of fluid for UV treatment. The device 10 has an inlet 12, an outlet 14, and a treatment chamber 16. The inlet 12 may receive water from a water tank, an intermediate holding tank or reservoir, or other water source. The outlet 14 may deliver water to a sink faucet, to a beverage maker, to an intermediate water holding reservoir, to a toilet for flushing, or to any other location that may benefit from receiving treated water. The inlet 12 and outlet 14 may have fittings 18 that allow the device to be installed with respect to current water line architecture. The treatment chamber 16 is provided as having a length and circumference sufficient to allow a desired amount of water to be treated. In one example, the chamber 16 can receive and treat/disinfect water at a flow rate of about five gallons of water per minute. However, faster or slower treatment rates are possible. Other examples include about one gallon per minute up to about 10 gallons per minute. The device 10 may be installed at the point of use for the treated water. For example, it may be installed within a sink cabinet. The device 10 may be the last flow through system through which the water travels before the water exits the faucet or other exit point feature.

Figure 2:
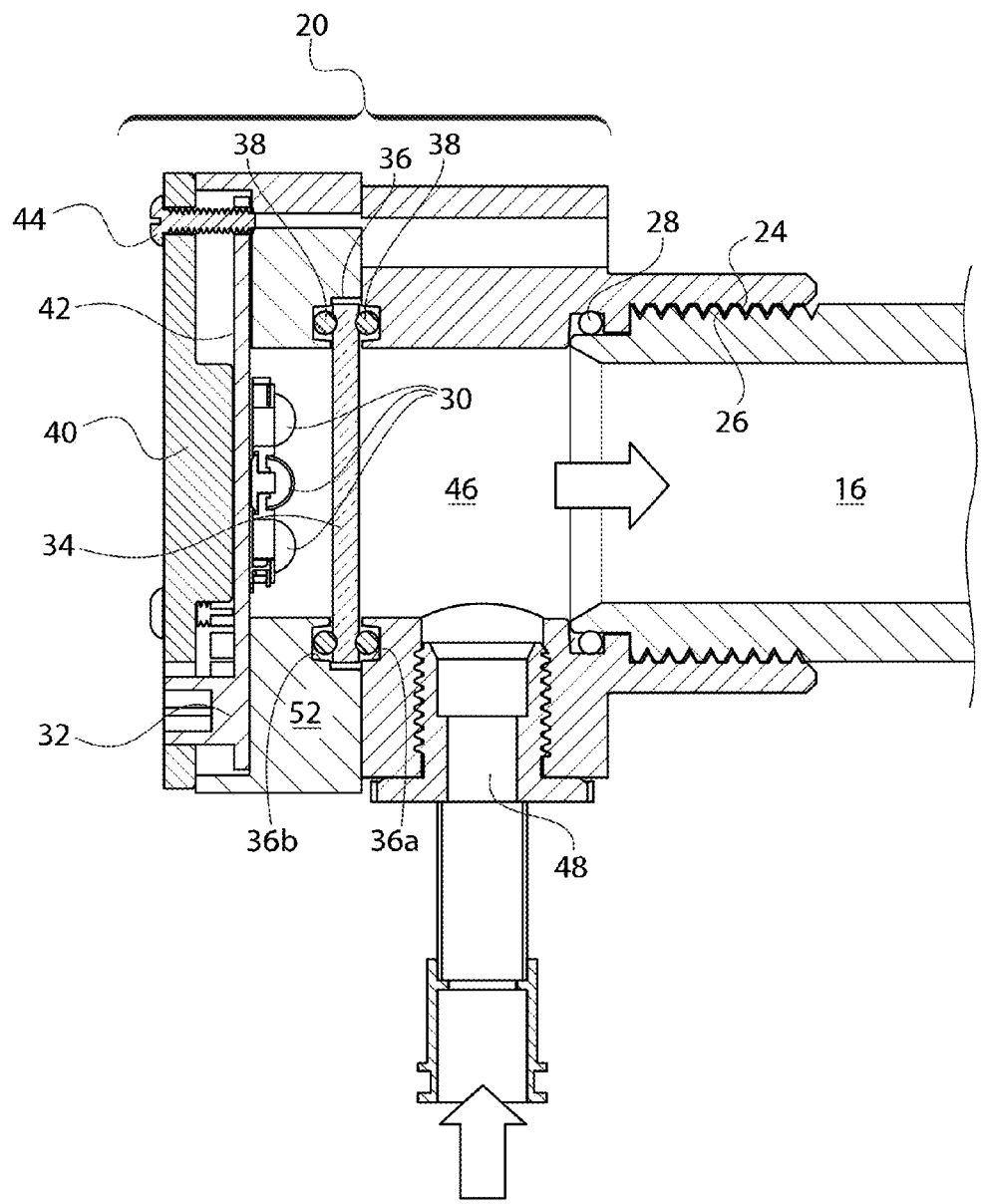
FIG. 2 shows a close-up side cross-sectional view of an end cap of the water treatment device of FIG. 1.

The device 10 may be formed via two end caps 20 and a treatment chamber 16, with one end cap 20 mounted on each end of the treatment chamber 16. The two end caps 20 are generally similar in structure, such that only one end cap 20 is described in detail. As shown in FIG. 2, each end cap 20 may have a connection portion 24 that cooperates with a corresponding connection portion 26 on the treatment chamber 16. This allows the end caps 20 to be removed and replaced when any component of the end cap 20 needs repair or replacement. This also allows an easy replacement for the treatment chamber 16 if need be. The connection portions 24, 26 can allow the device 10 to be modular. The end caps 20, along with the components mounted and housing within the end caps, can be removed and replaced. This can reduce the costs and time that would otherwise be required if an entirely new device 10 needed to be installed. One or more sealing features 28 may be provided at the interface between the end cap 20 and the treatment chamber 16 in order to prevent leakage, as well as to dampen vibrations.

The end cap 20 is provided to support one or more ultraviolet light emitting diodes 30 (UV LED). The UV LEDs 30 may be positioned in any arrangement or array with respect to a printed circuit board 32 (PCB). The UV LEDs emit ultraviolet light having a wavelength that will disrupt bacteria in order to disinfect the water being treated. In a specific example, the wavelength of the light emitted may be between about 200-400 nm. In a particular embodiment, the wavelength of the light emitted may be between about 250-270 nm. In an even more particular embodiment, the wavelength of the light emitted may be about 254 nm.

The UV LEDs 30 are mounted or otherwise positioned so that as water passes through the treatment chamber 16, UV rays are admitted and absorbed into the water stream. When UV energy is absorbed by the reproductive mechanisms of bacteria and viruses, the genetic material (DNA/RNA) is rearranged so that they can no longer reproduce, killing the bacteria and eliminating the risk of disease. UV treatment thus disinfects water without adding disinfection chemicals.

The UV LEDs 30 may be positioned in any desired configuration. One example is the array shown in FIG. 5. In this embodiment, the UV LEDs are arranged in a box-like outline having four corners and an interior UV LED therebetween. In another embodiment, the UV LEDs may be arranged in a circular configuration. In another embodiment, the UV LEDs may be arranged in a line configuration, such as rows. In another embodiment, the UV LEDs may be scattered in a random pattern. Alternate configurations are possible and within the scope of this invention. It has been found that, in one example, the UV LEDs 30 may be shaped to align with the shape of the treatment chamber. In this aspect, if the treatment chamber has a cylindrical or round cross-section, then the UV LEDs may be positioned in a circle. If the treatment chamber is square-shaped, then the UV LEDs may be positioned in a square, and so forth.

In the embodiment shown, there are five UV LEDs in the array, but it should be understood that fewer or more UV LEDs may be used, limited only by space and power requirements. The number and type of UV LEDs used may be dependent upon the energy needed for the flow rate treatment desired.

The UV LEDs may be secured with respect to the PCB 32 in any appropriate manner. For example, they may be welded into openings in the PCB, they may be secured via adhesive, they may be press fit into place, or any other appropriate securement method.

A shield 34 may be provided in order to provide a protective barrier between the UV LEDs 30 and the water flow F. The shield 34 may be formed of any appropriate material that will allow passage of the desired UV light wavelength therethrough. In one embodiment, the shield 34 may be quartz glass. In another embodiment, the shield 34 may be fused silica. In one embodiment, the shield 34 may be a polymeric material. Non-limiting examples include fluoroethylenepropylene (FEP), polytetrafluoroethylene (PTFE), or any other appropriate rigid material having a high UV emissivity level. It is possible for one or more coatings to be provided on shield. There may include, for example, coatings that prevent water or scale build-up, coatings that prevent bacteria build-up, or any other type of desired coating. The general properties of the shield 34 are such that the shield allows UV light to pass through easily, without substantially degrading or retarding the light path. The general goal is that the UV light passes uninterrupted past the shield 34. The shield also protects the UV LEDs 30 from contacting the water to be treated.

The shield 34 may have its ends inserted into a groove 36 in the end cap 20 as shown. In another embodiment, the shield may be soldered, welded, pinned, glued, friction fit, or secured into place using any other appropriate method. In one example, there are sealing features, such as o-rings 38, provided on one or both sides of the shield 34. This can prevent leakage. This can also prevent any vibrations from interfering with the integrity of shield 34.

At the end of each end cap 20 is a heat sink 40. The heat sink 40 is provided to manage heat that is generated by the UV LEDs 30. The heat sink 40 is used to dissipate the heat. Heat sink 40 may be any appropriate material. Non-limiting examples include copper, copper-tungsten or other copper alloys, aluminum, aluminum alloys, diamond or a diamond alloy (such as Dymalloy, a diamond in copper-silver alloy matrix), beryllium oxide, or any other appropriate heat-receiving/heat dissipating material. The heat sink 40 can prevent the heat generated from disturbing surrounding equipment. The heat sink 40 may be any appropriate size. The larger the surface area, the more heat dissipation, but there is also a balance between size and weight and efficiency onboard vehicles. Accordingly, in one aspect, the heat sink approximates the size of the end cap 20 as shown. The heat sink 40 may also be any appropriate shape. In one aspect, the heat sink 40 can be shaped similarly to the end cap. In one aspect, the heat sink 40 can be shaped to correspond to the cross-sectional shape of the treatment chamber 16. For example, if the treatment chamber 16 is tubular, then the heat sink 40 may have a circular shape 40.

An optional thermal paste may be applied on or around the heat sink 40. This may help weight and costs savings, as the thermal paste does not take up space or substantial weight, but it can increase the heat transfer of the heat sink 40. For example, the thermal paste may act as a heat catalyst to transfer heat to the heat sink 40, which can allow the physical size of the heat sink 40 to be smaller and/or lighter. In a specific configuration, the UV LEDs 30 may be mounted to the PCB board 32. A layer of thermal paste (not visible in the figures) may be applied to a back surface 42 of the PCB 32. The heat sink 40 may then be secured into place. Fixation members 44 are shown in FIGS. 1 and 2.

The treatment chamber 16 is mounted between two end caps 20. The chamber 16 may be cylindrical in cross-section and tubular in shape, as shown. It should be understood, however, that the chamber may be any desired shape, length, width or height. The reaction chamber 16 itself may be manufactured of any appropriate material, non-limiting examples of which include stainless steel, reinforced/composite material, aluminum, polymers, fluoroethylenepropylene (FEP), polytetrafluoroethylene (PTFE), carbon fiber, carbon fiber-reinforced polymer or carbon fiber-reinforced plastic (CFRP or CRP), polyetheretherketone (PEEK), coated or anodized aluminum, acrylonitrile butadiene styrene (ABS), glass-reinforced plastic (GRP), perfluoralkoxy (PFA), ethylenetetrafluoroethylene copolymer (ETFE), combinations thereof, or any other appropriate material having structural integrity and approved for drinking water contact. In one example, the treatment chamber 16 has a smooth surface finish of aluminum. In this example, the material may be treated to prevent oxidation and/or anodization. The treatment chamber 16 may be an non-transparent material, such that light does not escape the treatment chamber. (This can be for safety reasons, as well as for efficiency reasons.)

The treatment chamber 16 may have an optional surface coating of PTFE or Teflon, which can help reflect UV light better. The treatment chamber 16 may have a mirrored or otherwise shiny surface to help reflect UV light better. Providing a chamber 16 with a good reflective index prevents the chamber from absorbing the UV light, creates an environment where the light is reflected back to the water to be treated.

Figures 3, 4:
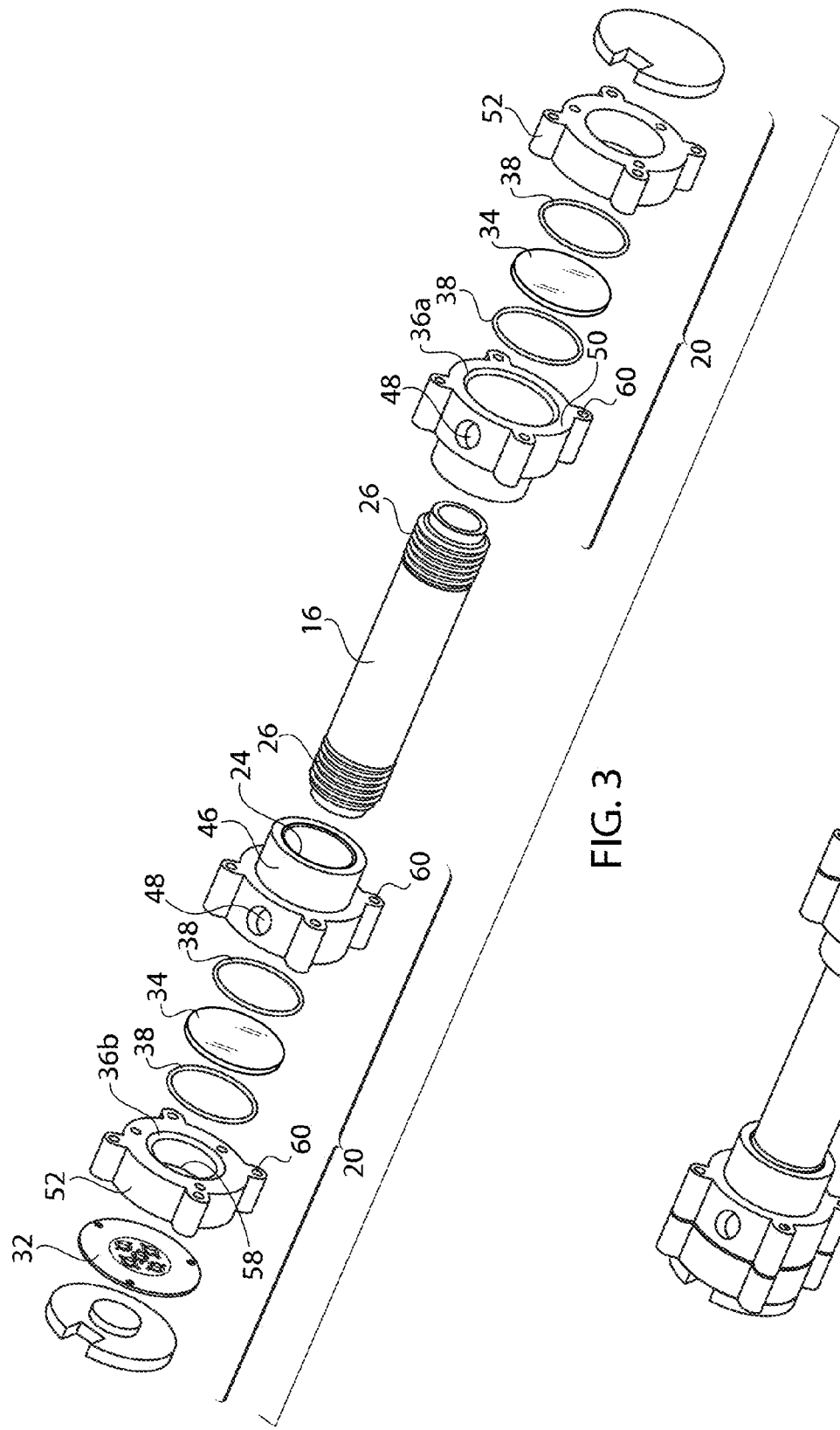
FIG. 3 shows an exploded view of a water treatment device.
FIG. 4 shows a side perspective view of the water treatment device of FIG. 3.

As shown in FIG. 3, the ends of the treatment chamber 16 may be threaded connection portions 26. These connection portions 26 cooperate with an internal corresponding thread receiving connection portion 24 on each end cap 20. It should be understood that the connection portions 24, 26 may be reversed and that other possible connection features may be used. The exploded view of FIG. 3 also illustrates the o-rings 38 and the shield 34, prior to being secured into place. This view also shows that the end caps 20 may be formed from two components. A first component may be an inlet/outlet support member 46 having an opening 48 for supporting the inlet component 12 and/or an outlet component 14. As shown in FIG. 2, the support member 46 may also have a first groove portion 36a at its outer face 50. The end cap 20 may also include a rear cap 52. This rear cap 52 may have a second groove portion 36b at its inner face 54. The shield 34 may be housed between the member 46 and the rear cap 52. As shown in FIGS. 1 and 2, the shield 34 may be positioned between the grooves 36a, 36b, such that each groove supports an o-ring 38 for securing the shield 34 into place.

Figure 5:
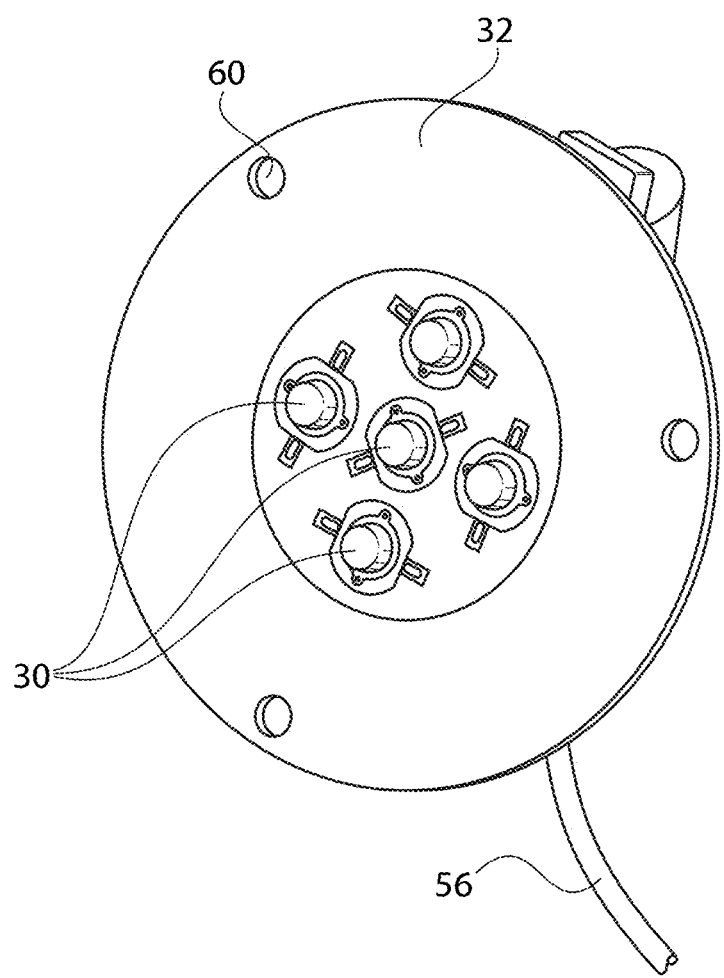
FIG. 5 shows a front perspective view of printed circuit board with ultraviolet LEDs positioned thereon.

Behind the rear cap 52 may be the PCB 32 supporting the one or more UV LEDS 30. As shown in FIG. 5, there may be an electrical connection 56 from the PCB 32 to an electric power source. The UV LEDs are received through an opening 58 in the rear cap 52. The member 46, the rear cap 52, and the PCB 32 may be secured to one another via one or more fixation members 44 that may extend through one or more securement openings 60, shown on a perimeter of the member 46, the rear cap 52, and the PCB 32.

The heat sink 40 is secured at the rear of the device 10. The heat sink is in contact with the PCB 32, such that is can absorb and dissipate heat therefrom.

In another embodiment, the UV LEDs may be organic LEDs (OLED). In one example, the OLEDs are not restricted by shape. They may be positioned at the end caps 20 or they may be positioned in a fine tube that runs within the treatment chamber 16. In one example, the water may be carried in a helical shape, and the OLED may be positioned along the helix. This means that continuous light can be delivered to the water.

Water may be treated as follows. A water flow F may enter the device at inlet 12. Inlet 12 may be secured to an on-board water line. Water entering the inlet passes into the treatment chamber. UV light from each set of UV LEDs 30 contacts the water in the treatment chamber 16 and helps to disinfect it. This configuration allows the water to be bombarded with UV light from the left and the right (or from the top and the bottom, depending upon in which direction the device is mounted) as it passes through the device 10. Water then leaves the treatment chamber through outlet 14. The outlet 14 may be is fluid communication with a faucet that delivers water to an end user.

The device 10 may be mounted in an under-the-sink cabinet. The device 10 may be mounted externally to a cabinet, but along a point of use water line. The device 10 may be mounted along hooks on the water line, such that the device can be pressed into place. The device 10 may be provided with an interface plate that can be mounted as desired.

The device 10 should be able to work with an aircraft power supply. This may be 400 Hz, using the aircraft engine supply. The device may work using 28V or 12V or any other appropriate voltage on-board a vehicle or aircraft.

The device 10 can run on-demand (when the water starts running), the diodes may be on stand-by, or the system may be continuously run. These options can allow the system to be more energy-efficient.

Depending upon the number of diodes used, there may be only a selective number that power on. In one example, if there are ten or twenty UV LEDs, only a portion may be activated, depending upon water flow rate and/or a pre programmed power-up sequence.

The use of UV LEDs can also allow the use of varying wavelengths. It is possible to choose and arrange a series of LEDs having varying wavelengths in the germicidal range (about 240 nm up to about 400 nm), without requiring all LEDs to be at the same exact wavelength. The LEDs may also be tunable to a certain wavelength.

Changes and modifications, additions and deletions may be made to the structures and methods recited above and shown in the drawings without departing from the scope or spirit of the invention and the following claims.

What is claimed is:

1. A water treatment device, comprising:
   a treatment chamber;
   a first set of ultraviolet light emitting diodes positioned at one end of the treatment chamber, and a second set of ultraviolet light emitting diodes positioned at an opposite end of the treatment chamber;
   each of the first and second sets of ultraviolet light emitting diodes being supported by first and second end caps;
   the first end cap comprising an inlet for receiving water to be treated, the second end cap comprising an outlet for exit of treated water;
   each of the end caps further supporting a shield secured in front of the ultraviolet light emitting diodes, the shield allowing UV light to pass through, and a heat sink secured behind the ultraviolet light emitting diodes.

2. The water treatment device of claim 1, wherein each of the first and second end caps comprises a support member and a rear cap.

3. The water treatment device of claim 1, wherein the treatment chamber comprises a mirrored or shiny reflective surface along its interior.

4. The water treatment device of claim 1, wherein the treatment chamber has a first connecting portion and wherein the end caps each have a second connecting portion.

5. The water treatment device of claim 4, wherein one of the first or second connecting portion comprises a threaded portion and wherein the other of the first or second connection portions comprises a thread receiving portion.

6. The water treatment device of claim 1, wherein the end caps form a groove for supporting the shield.

7. The water treatment device of claim 6, wherein the end cap comprises (i) a first portion containing a first portion of a groove on its rear face and (ii) a rear portion comprising a second portion of a groove on its front face, wherein when the first portion and the rear portion are secured to one another, the first and second portions of a groove collectively form a groove for supporting the shield.

8. The water treatment device of claim 1, further comprising at least one sealing element between each of the end caps and the treatment chamber.

9. The water treatment device of claim 1, further comprising at least one sealing element between each of the end caps and the shield.

10. The water treatment device of claim 1, wherein the first and second sets of ultraviolet light emitting diodes positioned are mounted on first and second printed circuit boards.

11. The water treatment device of claim 10, further comprising a thermal paste between the heat sink and the printed circuit boards.

12. The water treatment device of claim 1, wherein the first and second sets of ultraviolet light emitting diodes comprise organic light emitting diodes.

* * * * *